US012241876B1

(12) United States Patent
Feng et al.

(10) Patent No.: US 12,241,876 B1
(45) Date of Patent: Mar. 4, 2025

(54) BOREHOLE WALL SPIN-SHEARING DEVICE AND TESTING METHOD FOR IN-SITU BOREHOLE SHEAR TEST

(71) Applicants: Chengdu University Of Technology, Chengdu (CN); Guangdong Eagler Geological Equipment Technology CO., LTD., Zhuhai (CN)

(72) Inventors: Wenkai Feng, Chengdu (CN); Xiaoyu Yi, Chengdu (CN); Xuyong Liu, Zhuhai (CN); Yihe Li, Chengdu (CN); Qian Li, Chengdu (CN); Ke Wan, Chengdu (CN)

(73) Assignees: Chengdu University Of Technology, Chengdu (CN); Guangdong Eagler Geological Equipement Technology CO., LTD., Zhuhai (CN)

( * ) Notice: Subject to any disclaimer, the term of this patent is extended or adjusted under 35 U.S.C. 154(b) by 0 days.

(21) Appl. No.: 18/793,978

(22) Filed: Aug. 5, 2024

(30) Foreign Application Priority Data

Nov. 8, 2023 (CN) .......................... 202311474432.1

(51) Int. Cl.
*G01N 3/24* (2006.01)
*E21B 49/00* (2006.01)
*G01N 33/24* (2006.01)

(52) U.S. Cl.
CPC ............ *G01N 3/24* (2013.01); *E21B 49/006* (2013.01); *G01N 33/24* (2013.01); *G01N 2203/0025* (2013.01)

(58) Field of Classification Search
CPC .. G01N 3/24; G01N 33/24; G01N 2203/0025; G01N 9/00; G01N 3/02;

(Continued)

(56) References Cited

U.S. PATENT DOCUMENTS

| 4,458,525 A * | 7/1984 | Lutenegger ........... E21B 49/006 73/84 |
| 2020/0109533 A1* | 4/2020 | Mulla ...................... G01N 3/34 |

FOREIGN PATENT DOCUMENTS

| CN | 102944486 A | 2/2013 |
| CN | 104458445 A | 3/2015 |

(Continued)

OTHER PUBLICATIONS

Feng Wen-Kai, et al., In-situ Borehole Shear Test and Its Application in Residual Slope Soil, Science Technology and Engineering, 2017, pp. 289-293, vol. 17 No.34.

(Continued)

*Primary Examiner* — Brandi N Hopkins
(74) *Attorney, Agent, or Firm* — Bayramoglu Law Offices LLC

(57) ABSTRACT

A borehole wall spin-shearing device includes a load applying assembly, a soil shearing assembly, and a data acquisition assembly, where the load applying assembly is configured to apply a vertical load and an axial rotational load to the soil shearing assembly; the soil shearing assembly includes a plurality of shear plates; the plurality of shear plates are configured to penetrate into undisturbed soil after being ejected due to the vertical load and then shear the undisturbed soil due to the axial rotational load; and the data acquisition assembly is configured to acquire torque values of the plurality of shear plates during a process of shearing the undisturbed soil. The borehole wall spin-shearing device can directly conduct an in-situ borehole shear test in an exploration borehole with a conventional diameter in China, reducing the cost of drilling. The borehole wall spin-shearing device achieves a high degree of automation throughout the test.

11 Claims, 6 Drawing Sheets

(58) Field of Classification Search
CPC ..... G01N 29/07; E21B 49/006; E21B 33/063; E21B 29/08; E21B 7/061; E21B 17/1021; E21B 23/00; E21B 47/14; E21B 49/00; E21B 43/10; G01V 1/50; G01V 1/44; G01V 1/52; G01V 1/46; G01V 1/053; G01V 1/42; G01V 1/48; G01V 1/284; G01V 1/116; G01V 1/005; G01V 1/306

See application file for complete search history.

(56) References Cited

FOREIGN PATENT DOCUMENTS

| | | | |
|---|---|---|---|
| CN | 104535488 | A | 4/2015 |
| CN | 105928803 | A | 9/2016 |
| CN | 105973720 | A | 9/2016 |
| CN | 106949953 | A * | 7/2017 ............... G01H 5/00 |
| CN | 108007798 | A | 5/2018 |
| CN | 108426789 | A | 8/2018 |
| CN | 211627239 | U | 10/2020 |
| CN | 212008169 | U | 11/2020 |
| CN | 112326459 | A | 2/2021 |
| CN | 113607573 | A | 11/2021 |
| CN | 113702211 | A | 11/2021 |
| CN | 114624126 | A | 6/2022 |
| CN | 115855689 | A | 3/2023 |
| GB | 2008473 | A | 6/1979 |
| JP | 2004314261 | A | 11/2004 |
| JP | 2007255012 | A | 10/2007 |
| JP | 2013094901 | A | 5/2013 |

OTHER PUBLICATIONS

Feng Ji, et al., Experimental study of the shear strength criterion of rock structural plane based on three-dimensional surface description, Reviews on Advanced Materials Science, 2022, pp. 673-686, vol. 61.

Feng Wen-Kai, et al., Application of In-situ Borehole Shear Test in Optimization of Slope Stability Evaluation, Science Technology and Engineering, 2018, pp. 234-238, vol. 18 No.4.

Liu Xin, et al., Design of borehole in-situ shear test system, Journal of Traffic and Transportation Engineering, 2023, pp. 154-164, vol. 23 No.4.

Shan Dong, et al., Calculating the Permanent Displacement of a Rock Slope Based on the Shear Characteristics of a Structural Plane Under Cyclic Loading, Rock Mechanics and Rock Engineering, 2020, pp. 4583-4598, vol. 53.

F. L. Pellet, et al., Shear behavior of the interface between drilling equipments and shale rocks, Journal of Petroleum Exploration and Production Technology, 2014, pp. 245-254, vol. 4.

* cited by examiner

BOREHOLE WALL SPIN-SHEARING DEVICE AND TESTING METHOD FOR IN-SITU BOREHOLE SHEAR TEST

CROSS REFERENCE TO THE RELATED APPLICATIONS

This application is based upon and claims priority to Chinese Patent Application No. 202311474432.1, filed on Nov. 8, 2023, the entire contents of which are incorporated herein by reference.

TECHNICAL FIELD

The present disclosure relates to the field of engineering survey, and in particular to a borehole wall spin-shearing device and testing method for an in-situ borehole shear test.

BACKGROUND

The shear strength of rock and soil is an important parameter for studying the mechanical properties of rock and soil and conducting engineering design. The commonly used methods for measuring the shear strength of rock and soil include indoor and on-site tests.

Indoor tests include direct shear tests and triaxial shear tests. The direct shear test features simple instrument structure and convenient operation. However, it cannot guarantee that the shear plane is the plane of the specimen with the weakest shear resistance or that the distribution of shear stress on the shear plane is even, thereby leading to inaccurate test results. In addition, during the shearing process, the shear area of the specimen gradually decreases, and the drainage conditions cannot be strictly controlled, making it hard to measure the changes in pore water pressure during the shearing process. The triaxial shear test features simple structure and convenient operation, and can strictly control the drainage conditions, measure the changes in pore water pressure, and demonstrate a clear stress state. However, it involves complex operation, a large number of specimens, fixed principal stress direction, and high requirements for specimen preparation, resulting in a limited usage range.

The on-site tests mainly include on-site shear tests, vane shear tests, and borehole shear tests. The on-site shear tests include push shear tests using a large shear apparatus, a jack or a horizontal extrusion method, and shear tests using a one-time horizontal shear method. The on-site shear test can be conducted on the rock and soil, along a weak structural plane of the rock and soil, and on the contact surface between rock and other materials. However, it has the disadvantages of difficult specimen preparation, large instrument size, long testing time, and high cost. The vane shear test can quickly determine the undrained shear strength of saturated clayey soil on site, but the applicability of the vane shear test is limited and it is only applicable for soft clay, rather than high-plasticity clayey soil and soil doped with gravel debris. The borehole shear test is an in-situ shear test conducted on the borehole wall through an extendable probe. The borehole shear test can provide strength data of soil or soft rock, and its biggest advantage lies in simple operation and high repeatability. Data shows that the results of the borehole shear test are very close to the consolidated undrained shear parameters. However, the shear probes used by existing borehole shear equipment are developed by foreign companies. Since the borehole diameters in foreign countries are much smaller than those of conventional exploration boreholes in China, additional boreholes need to be drilled before testing, which is time-consuming and labor-intensive. In addition, the tooth spacing of existing shear probes is relatively small, which may fail to fully penetrate the soil during testing, thereby leading to errors in test results.

Overall, the methods for measuring the shear strength of soil in the prior art all have some drawbacks and limitations in use. They are not applicable to homogeneous soil, inhomogeneous soil such as coarse-grained soil (gravel), as well as soft rocks such as mudstone.

SUMMARY

The present disclosure aims to solve the above-mentioned problem in the prior art, that is, the commonly used methods for measuring the shear strength of soil are not applicable for homogeneous soil, inhomogeneous soil such as coarse-grained soil (gravel), as well as soft rock such as mudstone. For this purpose, the present disclosure provides a borehole wall spin-shearing device and testing method for an in-situ borehole shear test.

In order to achieve the above objective, the present disclosure adopts the following technical solutions. The present disclosure provides a borehole wall spin-shearing device for an in-situ borehole shear test, including a load applying assembly, a soil shearing assembly, and a data acquisition assembly, where
  the load applying assembly is configured to apply a vertical load and an axial rotational load to the soil shearing assembly;
  the soil shearing assembly includes a plurality of shear plates; and the plurality of shear plates are configured to penetrate into undisturbed soil after being ejected due to the vertical load and then shear the undisturbed soil due to the axial rotational load; and
  the data acquisition assembly is configured to acquire torque values of the plurality of shear plates during a process of shearing the undisturbed soil.

In the present disclosure, the borehole wall spin-shearing device for an in-situ borehole shear test is designed based on the following principle. The load applying assembly applies the vertical load and the axial rotational load to the shear plates, such that the shear plates fully penetrate into the undisturbed soil, allowing the shear plates to fully contact with the undisturbed soil, thereby reducing test data errors. The spacing between the shear plates in the soil shearing assembly is larger than that of an existing borehole shear instrument, making the borehole wall spin-shearing device suitable for homogeneous soil, inhomogeneous soil such as coarse-grained soil (gravel), as well as soft rocks such as mudstone. The data acquisition assembly acquires the torque values of the shear plates during the process of shearing the undisturbed soil, and calculates the shear strength parameter of the undisturbed soil.

Further, as a specific design of the load applying assembly, the load applying assembly includes a drilling rig; and the drilling rig includes a drill rod and a servo motor located at a top of the drill rod;
  the soil shearing assembly is connected to a bottom of the drill rod through a drill rod joint; and an output end of the servo motor is connected to the top of the drill rod; and
  the drill rod and the servo motor are respectively configured to apply the vertical load and the axial rotational load to the soil shearing assembly.

Further, as a specific design of the soil shearing assembly, the soil shearing assembly further includes a shear cylinder in a hollow cylindrical structure; a spinning shaft is provided in the shear cylinder and is vertically movable; an upper half of the spinning shaft forms a cylindrical structure; and a top on the upper half of the spinning shaft is provided with the drill rod joint;
- a lower half of the spinning shaft forms a conical structure with a tip facing downwards;
- the spinning shaft is slidably connected to the shear cylinder;
- a bottom circumferential outer wall of the shear cylinder is provided with a circular receiving groove; four shear plates centered on an axis of the shear cylinder are circumferentially evenly spaced in the circular receiving groove; each of the shear plates is in a curved plate structure; a length direction of the shear plates is identical to a length direction of the shear cylinder; the four shear plates enclose a cylindrical structure; and an axis of the cylindrical structure coincides with the central axis of the shear cylinder;
- an inner curved surface of each shear plate facing the central axis of the shear cylinder protrudes to form a connecting piece; the connecting piece forms a trapezoid-like structure with a small upper end and a large lower end; an inner side of the connecting piece is provided with a fitting groove with a T-shaped cross-section along a length direction of the connecting piece; and a gradient of the inner side of the connecting piece is equal to a generatrix inclination of the lower half of the spinning shaft;
- four notches are arranged at a bottom of the circular receiving groove for partial passage of the four connecting pieces; and the inner side of the connecting piece passes through the notch to be located inside the shear cylinder;
- a conical surface on the lower half of the spinning shaft is provided with four guide rail strips that are circularly spaced around an axis of the spinning shaft; and a length direction of each of the guide rail strips is oriented from a major-diameter end on the lower half of the spinning shaft towards a minor-diameter end on the lower half of the spinning shaft; and
- each of the guide rail strips is provided with a T-shaped cross-section and matched with one connecting piece; and the guide rail strip is slidably provided in the fitting groove.

Further, a plurality of limit bars are circularly evenly spaced on a circumferential outer wall on the upper half of the spinning shaft within the shear cylinder; and the plurality of limit bars are detachably connected to the circumferential outer wall on the upper half of the spinning shaft; and
- the shear cylinder is provided with two open ends; a circumferential inner wall of the shear cylinder is provided with a plurality of limit slots that are slidably matched with the plurality of limit bars; and the limit bars and the limit slots are arranged along an axial direction of the spinning shaft.

Further, a top opening of the shear cylinder is provided with a limit flange; and an inner ring diameter of the limit flange is greater than a diameter of the upper half of the spinning shaft and smaller than an inner diameter of the shear cylinder.

Further, a bottom opening of the shear cylinder is provided with a rebound assembly; the rebound assembly includes a spring sleeve; the spring sleeve includes a top end with an opening and a closed bottom end; a top of the spring sleeve is connected to a bottom of the shear cylinder; a reset spring is provided in the spring sleeve; a bottom end of the reset spring is fixedly connected to an inner bottom side of the spring sleeve; and a top of the reset spring is fixed to a push plate; and
- when the drill rod presses downwards, the lower half of the spinning shaft is driven to pass through the top opening of the spring sleeve to contact an upper end face of the push plate.

Further, a bottom of the spring sleeve is provided with a rotating base in a cylindrical structure; an axis of the rotating base coincides with an axis of the spring sleeve; a threaded cylindrical pin is provided in the spring sleeve; an axis of the threaded cylindrical pin coincides with the axis of the spring sleeve; a threaded end of the threaded cylindrical pin passes through the bottom end of the spring sleeve and is matched with a center thread of the rotating base; a plain shaft portion of the threaded cylindrical pin is rotatably matched with the bottom end of the spring sleeve; and a thrust bearing is provided between the rotating base and the spring sleeve.

The present disclosure further provides a testing method for the borehole wall spin-shearing device for an in-situ borehole shear test, including the following steps:
- step 1: drilling, by the drilling rig, a borehole;
- step 2: calibrating the soil shearing assembly on a ground: applying, by the drill rod, the vertical load; and measuring, by the data acquisition assembly, load values required to eject the plurality of shear plates;
- step 3: driving, by the drill rod, the soil shearing assembly to a preset test depth in the borehole, such that a bottom of the soil shearing assembly comes into contact with soil at a bottom surface of the borehole;
- step 4: continuously pressing the drill rod downwards to apply the vertical load to the plurality of shear plates in the soil shearing assembly, such that the plurality of shear plates are ejected due to the vertical load and fully penetrate into the undisturbed soil;
- step 5: keeping the vertical load constant; starting the servo motor, such that the plurality of shear plates rotate to conduct a borehole wall spin-shearing test; and stopping the test after the plurality of shear plates rotate 90°; and
- step 6: performing, by the data acquisition assembly including a torque sensor and a pressure sensor, the following operations:
- acquiring, by the torque sensor, maximum torques applied to the plurality of shear plates during the borehole wall spin-shearing test; acquiring, by the pressure sensor, maximum normal forces received by the plurality of shear plates; and calculating a shear strength parameter of the undisturbed soil based on the maximum torques and the maximum normal forces.

Further, in the step 6, the shear strength parameter of the undisturbed soil is calculated as follows:

$$\tau_{max} = \frac{4M_{T_{max}}}{\pi D^2 h}$$

where, $\tau_{max}$ denotes a maximum shear stress of the undisturbed soil, kPa; $M_{T_{max}}$ denotes a maximum torque applied to a single shear unit, kN·m; and D and h respectively denote a diameter and height of a circular arc formed by the rotation of the plurality of shear plates ejected, m;

at a same depth in four adjacent boreholes, maximum shear stresses of the undisturbed soil at the same depth in four different boreholes are expressed as $\tau_{max1}$–

$\tau_{max4}$, and the maximum normal forces acquired by the pressure sensor are expressed as $\sigma_{nmax1}$–$\sigma_{max4}$;

$$\tau_{max}=c+\sigma_{nmax} \tan \varphi$$

the maximum normal forces $\sigma_{nmax}$–$\sigma_{nmax4}$ are measured in kPa; a curve is plotted with the maximum normal force $\sigma_{nmax}$ as an x-axis and the maximum shear stress $\tau_{nmax}$ as a y-axis; and c and φ are acquired through curve fitting; c denotes cohesion, kPa; φ denotes an internal friction angle; and the cohesion and the internal friction angle are the shear strength parameters of the undisturbed soil.

The present disclosure has the following beneficial effects. The present disclosure can directly conduct an in-situ borehole shear test in an exploration borehole with a conventional diameter in China, reducing the cost of drilling. The present disclosure can mechanically accurately apply a vertical load, ensuring the penetration of the shear plates into undisturbed soil and ensuring test accuracy. The present disclosure reduces the impact of borehole wall collapse on the borehole shear test and eliminates the frictional force between the soil at the bottom of the borehole and the bottom of the shear probe. The present disclosure achieves a high degree of automation throughout the test and can quickly and accurately derive the shear strength parameter of undisturbed soil.

Figure 1:
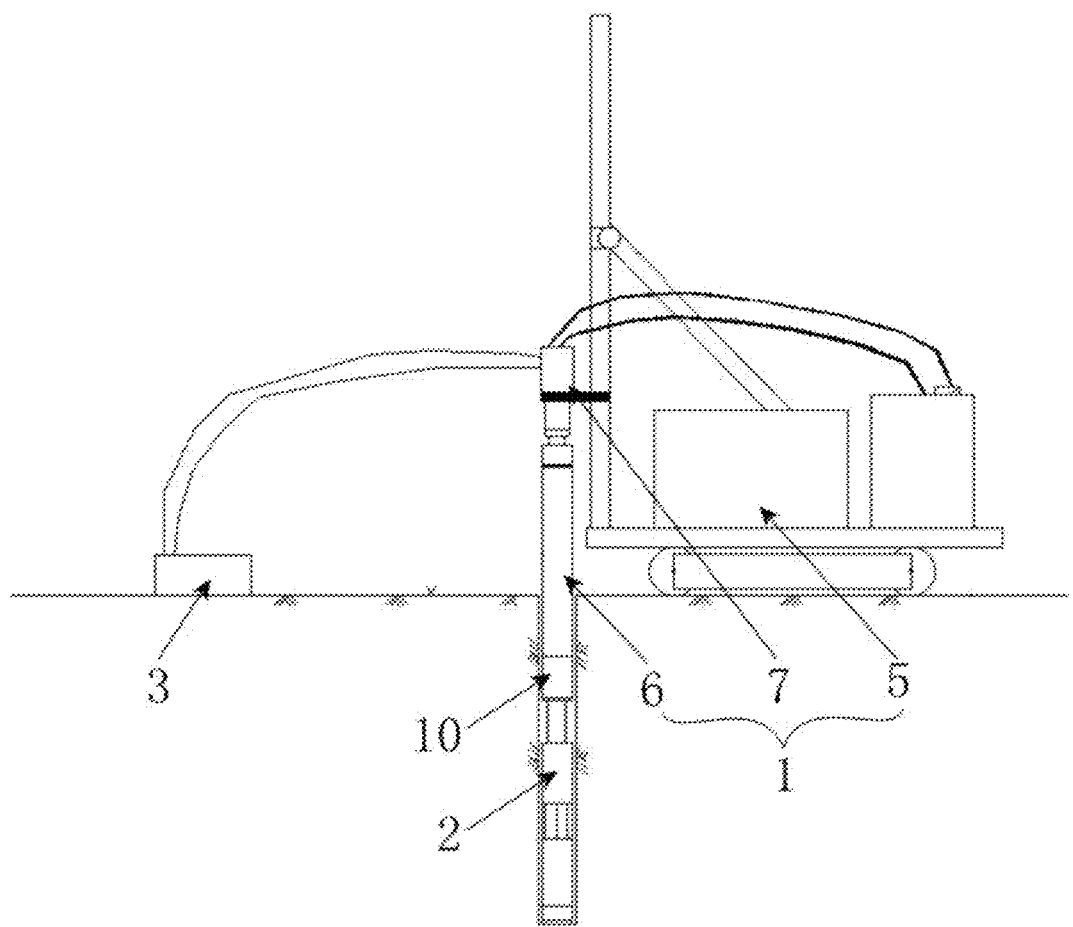
FIG. 1 is a structural diagram of a borehole wall spin-shearing device for an in-situ borehole shear test.

Reference Numerals: 1. load applying assembly; 2. soil shearing assembly; 3. data acquisition assembly; 4. shear plate; 5. drilling rig; 6. drill rod; 7. servo motor; 8. shear cylinder; 9. spinning shaft; 10. drill rod joint; 11. circular receiving groove; 12. connecting piece; 13. fitting groove; 14. notch; 15. guide rail strip; 16. limit bar; 17. limit slot; 18. limit flange; 19. rebound assembly; 20. spring sleeve; 21. return spring; 22. push plate; 23. rotating base; 24. threaded cylindrical pin; and 25. thrust bearing.

DETAILED DESCRIPTION OF THE EMBODIMENTS

The specific embodiment of the present disclosure will be described below so that those skilled in the art can understand the present disclosure, but it should be clear that the present disclosure is not limited to the scope of the specific embodiment. For those of ordinary skill in the art, as long as various changes fall within the spirit and scope of the present disclosure defined and determined by the appended claims, these changes are apparent, and all inventions and creations using the concept of the present disclosure are protected.

As shown in FIG. 1, the present disclosure provides a borehole wall spin-shearing device for an in-situ borehole shear test, including load applying assembly 1, soil shearing assembly 2, and data acquisition assembly 3.

The load applying assembly 1 is configured to apply a vertical load and an axial rotational load to the soil shearing assembly 2.

The soil shearing assembly 2 includes a plurality of shear plates 4. The plurality of shear plates 4 are configured to be ejected and penetrate into undisturbed soil after being subjected to the vertical load. The plurality of shear plates 4 penetrating into the undisturbed soil further shear the undisturbed soil after being subjected to the axial rotational load.

The data acquisition assembly 3 is configured to acquire torque values of the plurality of shear plates 4 during a process of shearing the undisturbed soil.

The load applying part can use drilling rig 5, a jack, or other devices. In this embodiment, preferably, the load applying assembly 1 uses drilling rig 5. Specifically, the load applying assembly 1 includes drilling rig 5. The drilling rig 5 includes drill rod 6 and servo motor 7 located at a top of the drill rod 6.

The soil shearing assembly 2 is connected to a bottom of the drill rod 6 through drill rod joint 10. An output end of the servo motor 7 is connected to the top of the drill rod 6. The drill rod 6 and the servo motor 7 are respectively configured to apply the vertical load and the axial rotational load to the soil shearing assembly 2.

Figure 2:
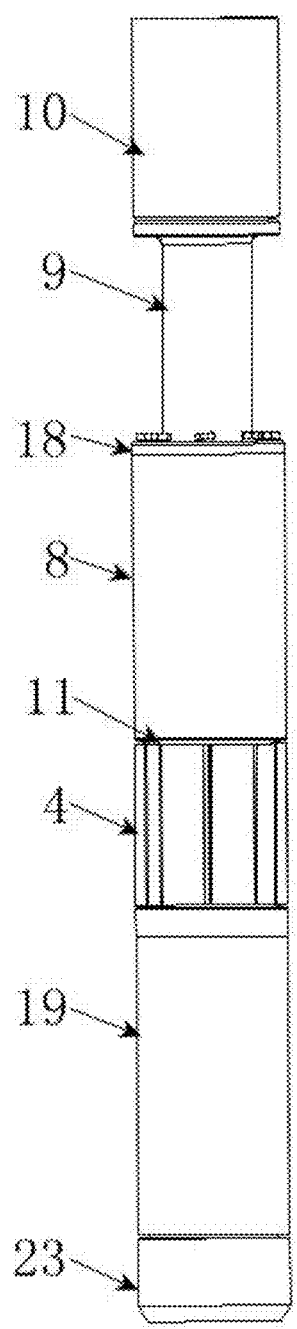
FIG. 2 is a three-dimensional structural diagram of a soil shearing assembly.
Figure 3:
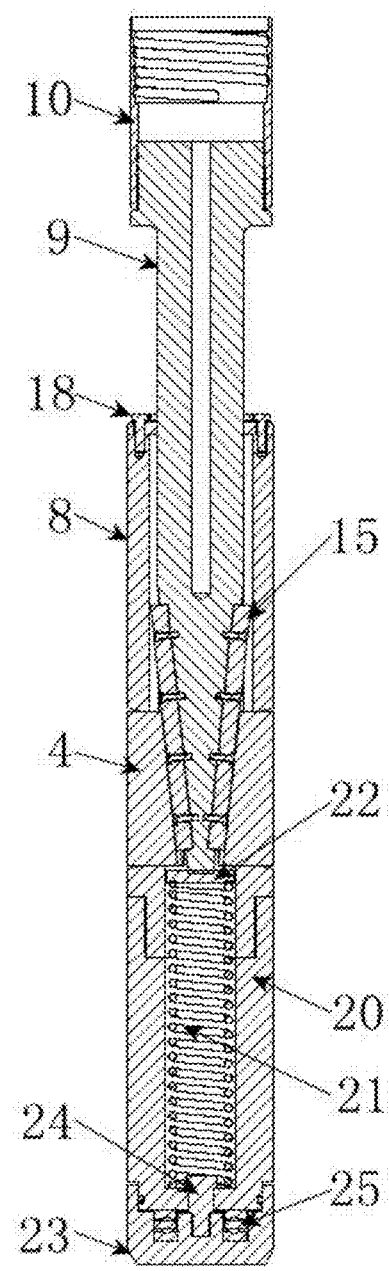
FIG. 3 is an internal structural diagram of the soil shearing assembly.

In this embodiment, as shown in FIGS. 2 and 3, as a specific design of the soil shearing assembly 2, the soil shearing assembly 2 further includes shear cylinder 8 in a hollow cylindrical structure. Spinning shaft 9 is provided in the shear cylinder 8 and is vertically movable. An upper half of the spinning shaft 9 forms a cylindrical structure, and a top on the upper half of the spinning shaft 9 is provided with the drill rod joint 10. A lower half of the spinning shaft 9 forms a conical structure with a tip facing downwards.

A bottom circumferential outer wall of the shear cylinder 8 is provided with circular receiving groove 11. The four shear plates 4 centered on an axis of the shear cylinder 8 are circumferentially evenly spaced in the circular receiving groove. Each of the shear plates 4 is in a curved plate structure, and a length direction of the shear plate 4 is identical to a length direction of the shear cylinder 8. The four shear plates enclose a cylindrical structure, and an axis of the cylindrical structure coincides with the central axis of the shear cylinder 8.

Figure 5:
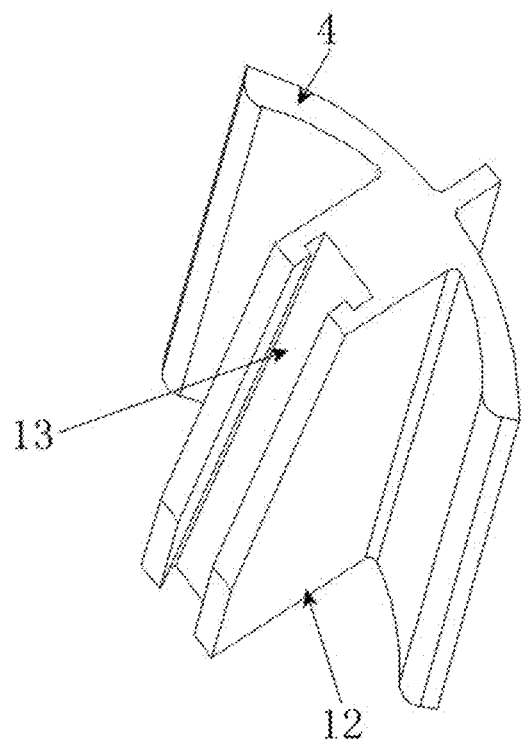
FIG. 5 is a structural diagram of a single shear plate.

As shown in FIG. 5, an inner curved surface of each shear plate 4 facing the central axis of the shear cylinder 8 protrudes to form connecting piece 12. The connecting piece 12 has a trapezoid-like structure with a small upper end and a large lower end. An inner side of the connecting piece 12 is provided with fitting groove 13 with a T-shaped cross-section along a length direction of the connecting piece. A gradient of the inner side of the connecting piece 12 is equal to a generatrix inclination of the lower half of the spinning shaft 9.

Four notches 14 are arranged at a bottom of the circular receiving groove 11 for partial passage of the four connecting pieces 12. The inner side of the connecting piece 12 passes through the notch 14 to be located inside the shear cylinder 8.

Figure 4:
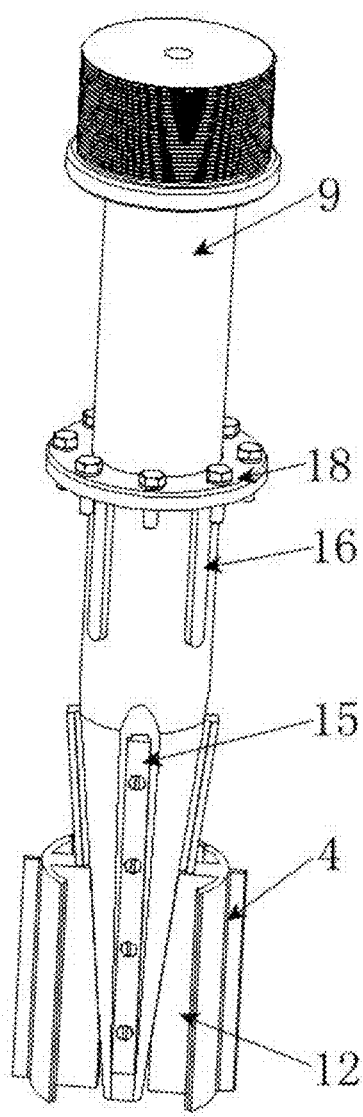
FIG. 4 is a structural diagram of a spinning shaft.

As shown in FIG. 4, a conical surface on the lower half of the spinning shaft 9 is provided with four guide rail strips 15 that are circularly spaced around an axis of the spinning shaft 9. A length direction of each guide rail strip 15 is oriented from a major-diameter end on the lower half of the spinning shaft 9 towards a minor-diameter end on the lower half of the spinning shaft 9.

Each guide rail strip 15 is provided with a T-shaped cross-section, and each guide rail strip 15 is matched with one connecting piece 12. The guide rail strip 15 is slidably provided in the fitting groove 13.

Before a borehole wall spin-shearing test is started, first, the spinning shaft 9 is fixedly connected to the bottom of the drill rod 6 through the drill rod joint 10, and the top of the drill rod 6 is connected to a power output shaft of the servo motor 7. Then, the entire soil shearing assembly 2 is lowered to a designated depth inside a borehole through the drilling rig 5 and the drill rod 6. A bottom of the soil shearing assembly 2 is in contact with soil at the bottom of the borehole. The drilling rig 5 drives the drill rod 6 to press downwards. The downwards pressing drill rod 6 transmits a force to the spinning shaft 9 through the drill rod joint 10. The spinning shaft 9 moves vertically and downwards relative to the shear cylinder 8. When the spinning shaft 9 moves vertically and downwards, the guide rail strips 15 on the conical surface on the lower half of the spinning shaft 9 are matched with the fitting grooves 13 of the connecting pieces 12 on the shear plates 4. As the spinning shaft 9 continues to move vertically and downwards, the shear plates 4 are ejected in a radial direction of the spinning shaft 9 until the shear plates 4 penetrate into undisturbed soil. Finally, the servo motor 7 is started to conduct the spin-shearing test. The servo motor 7 automatically stops rotating after the shear plates 4 rotate 90°, and the drilling rig 5 stops applying the vertical load. At this point, the data acquisition assembly 3 records, saves, and exports the complete torque value data saved in the data acquisition system during the shearing process.

Specifically, the data acquisition assembly 3 includes a controller, a torque sensor, and a pressure sensor that are connected to each other electrically. The torque sensor is located on the servo motor 7 to acquire the torque value applied by the servo motor 7 to the shear plate 4. The pressure sensor is located between the drill rod 6 and the soil shearing assembly 2 to acquire maximum normal force acting on the shear plate 4. The connection relationship and model of the electrical elements in the data acquisition assembly 3 are based on existing mature technologies, so the circuit structure and working principle of the electrical elements will not be elaborated herein.

Figure 6:
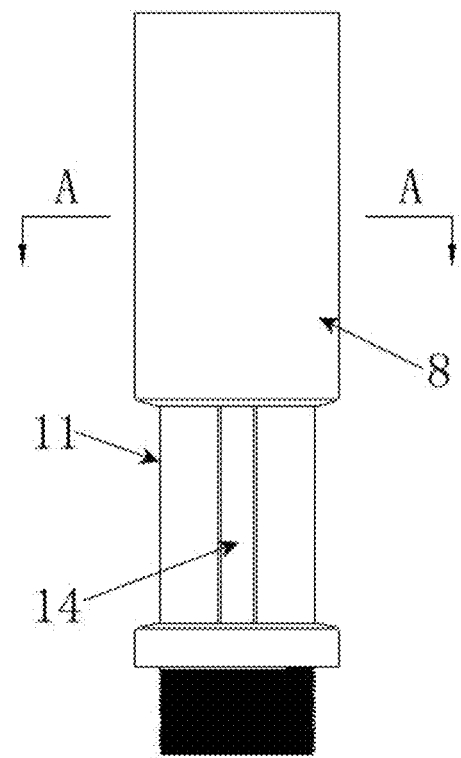
FIG. 6 is a structural diagram of a shear cylinder.
Figure 7:
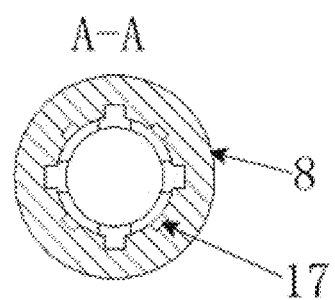
FIG. 7 is a structural diagram of the shear cylinder along direction A-A shown in FIG. 6.

Preferably, but not limited to, as shown in FIGS. 4, 6, and 7, a plurality of limit bars 16 are circularly evenly spaced on a circumferential outer wall on the upper half of the spinning shaft 9 within the shear cylinder 8. The plurality of limit bars 16 are detachably connected to the circumferential outer wall on the upper half of the spinning shaft 9. The shear cylinder 8 is provided with two open ends. A circumferential inner wall of the shear cylinder 8 is provided with a plurality of limit slots 17 that are slidably matched with the plurality of limit bars 16. The limit bars 16 and the limit slots 17 are arranged along an axial direction of the spinning shaft 9.

The limit bars 16 and the limit slots 17 are matched to limit the rotational freedom of the spinning shaft 9, such that the spinning shaft 9 can only be vertically displaced within the shear cylinder 8, thereby avoiding the rotation of the spinning shaft 9 relative to the shear cylinder 8.

In order to fix the spinning shaft 9 inside the shear cylinder 8 to avoid the spinning shaft 9 from detaching from the shear cylinder 8 during the shearing test, preferably, a top opening of the shear cylinder 8 is provided with limit flange 18. An inner ring diameter of the limit flange 18 is greater than a diameter of the upper half of the spinning shaft 9 and smaller than an inner diameter of the shear cylinder 8.

Preferably, but not limited to, a bottom opening of the shear cylinder 8 is provided with rebound assembly 19. The rebound assembly 19 includes spring sleeve 20. The spring sleeve 20 includes a top end with an opening and a closed bottom end. Atop of the spring sleeve 20 is connected to a bottom of the shear cylinder 8. A reset spring is provided in the spring sleeve 20. A bottom end of the reset spring is fixedly connected to an inner bottom side of the spring sleeve 20. A top of the reset spring is fixed to push plate 22. When the drill rod 6 presses downwards, the lower half of the spinning shaft 9 is driven to pass through the top opening of the spring sleeve 20 to contact an upper end face of the push plate 22 and compress return spring 21.

After the shearing test is completed, the drill rod 6 drives the soil shearing assembly 2 to pull upwards. At this point, the spinning shaft 9 moves upwards relative to the shear cylinder 8. Meanwhile, the return spring 21 pushes the spinning shaft 9 upwards. The upwards moving spinning shaft 9 contracts the four shear plates 4 back into the circular receiving groove 11, playing an active role in storing the shear plates 4. Due to the setting of the rebound assembly 19, the shear plate 4 has a certain distance from the soil at the bottom of the borehole, eliminating the impact of borehole wall collapse on the test accuracy.

Preferably, a bottom of the spring sleeve 20 is provided with rotating base 23 in a cylindrical structure. An axis of the rotating base 23 coincides with an axis of the spring sleeve 20. Threaded cylindrical pin 24 is provided in the spring sleeve 20. An axis of the threaded cylindrical pin 24 coincides with the axis of spring sleeve 20. A threaded end of the threaded cylindrical pin 24 passes through the bottom end of the spring sleeve 20 and is matched with a center thread of the rotating base 23. A plain shaft portion of the threaded cylindrical pin 24 is rotatably matched with the bottom end of the spring sleeve 20. Thrust bearing 25 is provided between the rotating base 23 and the spring sleeve 20. Through the above design, the rotating base 23 is rotatable relative to the bottom of the spring sleeve 20 without transmitting the torque to the spring sleeve 20. Therefore, during the shearing test, the impact of the frictional force between the soil at the bottom of the borehole and the soil shearing assembly 2 is eliminated, further improving the test accuracy.

The present disclosure further provides a testing method for the borehole wall spin-shearing device for an in-situ borehole shear test, including the following steps. Step 1. A borehole is drilled by the drilling rig 5.

Step 2. The soil shearing assembly 2 is calibrated on a ground. That is, the drill rod 6 applies a vertical load, and the data acquisition assembly 3 measures load values required to eject the plurality of shear plates 4.

Step 3. The drill rod 6 drives the soil shearing assembly 2 to a preset test depth in the borehole, such that a bottom of the soil shearing assembly 2 comes into contact with soil at a bottom surface of the borehole.

Step 4. The drill rod 6 continues to press downwards and apply a vertical load to the plurality of shear plates 4 in the soil shearing assembly 2. Due to the vertical load, the plurality of shear plates 4 are ejected and penetrate into undisturbed soil.

Step 5. The vertical load is kept constant. The servo motor 7 is started, and the plurality of shear plates 4 rotate to conduct a borehole wall spin-shearing test. The test stops after the plurality of shear plates 4 rotate 90°.

Step 6. The data acquisition assembly 3 includes a torque sensor and a pressure sensor.

The torque sensor acquires the maximum torque applied to the plurality of shear plates 4 during the borehole wall spin-shearing test, while the pressure sensor acquires the maximum normal force received by the plurality of shear plates 4, and calculates a shear strength parameter of the undisturbed soil based on the maximum torque and the maximum normal force.

Further, in the step 6, the shear strength parameter of the undisturbed soil is calculated as follows:

$$\tau_{max} = \frac{4M_{T_{max}}}{\pi D^2 h}$$

where, $\tau_{max}$ denotes a maximum shear stress of the undisturbed soil, kPa; $M_{Tmax}$ denotes a maximum torque applied to a single shear unit, kN·m; and D and h respectively denote a diameter and height of a circular arc formed by the rotation of the plurality of shear plates 4 ejected, m.

At a same depth in four adjacent boreholes, maximum shear stresses of the undisturbed soil at the same depth in four different boreholes are expressed as $\tau_{max1}$–$\tau_{max4}$, and maximum normal forces acquired by the pressure sensor are expressed as $\sigma_{nmax1}$–$\sigma_{nmax4}$.

$$\tau_{max} = c + \sigma_{nmax} \tan \varphi$$

The maximum normal forces $\sigma_{nmax1}$–$\sigma_{nmax4}$ are measured in kPa. A curve is plotted with the maximum normal force $\sigma_{nmax}$ as an x-axis and the maximum shear stress $\tau_{max}$ as a y-axis. c and φ are acquired through curve fitting. C denotes cohesion, kPa. φ denotes an internal friction angle. The cohesion and the internal friction angle are the shear strength parameters of the undisturbed soil.

In summary, the testing method can quickly carry out an in-situ borehole shear test while drilling, and automatically and accurately acquire the shear strength parameters of the undisturbed soil, meeting the requirements of quickly and accurately acquiring the shear strength parameters of the undisturbed soil.

The invention claimed is:

1. A borehole wall spin-shearing device for an in-situ borehole shear test, comprising a load applying assembly, a soil shearing assembly, and a data acquisition assembly, wherein
   the load applying assembly is configured to apply a vertical load and an axial rotational load to the soil shearing assembly;
   the soil shearing assembly comprises a plurality of shear plates; and the plurality of shear plates are configured to penetrate into undisturbed soil after being ejected due to the vertical load and then shear the undisturbed soil due to the axial rotational load; and
   the data acquisition assembly is configured to acquire torque values of the plurality of shear plates during a process of shearing the undisturbed soil; the load applying assembly comprises a drilling rig; and the drilling rig comprises a drill rod and a servo motor located at a top of the drill rod;
   the soil shearing assembly is connected to a bottom of the drill rod through a drill rod joint; and an output end of the servo motor is connected to the top of the drill rod;
   the drill rod and the servo motor are respectively configured to apply the vertical load and the axial rotational load to the soil shearing assembly; the soil shearing assembly further comprises a shear cylinder in a hollow cylindrical structure; a spinning shaft is provided in the shear cylinder and is vertically movable; an upper half of the spinning shaft forms a cylindrical structure; and a top on the upper half of the spinning shaft is provided with the drill rod joint;
   a lower half of the spinning shaft forms a conical structure with a tip facing downwards;
   the spinning shaft is slidably connected to the shear cylinder;
   a bottom circumferential outer wall of the shear cylinder is provided with a circular receiving groove; four shear plates centered on an axis of the shear cylinder are circumferentially evenly spaced in the circular receiving groove; each of the shear plates is in a curved plate structure; a length direction of the shear plates is identical to a length direction of the shear cylinder; the four shear plates enclose a cylindrical structure; and an axis of the cylindrical structure coincides with the central axis of the shear cylinder;
   an inner curved surface of each shear plate facing the central axis of the shear cylinder protrudes to form a connecting piece; the connecting piece forms a trapezoid-like structure with a small upper end and a large lower end; an inner side of the connecting piece is provided with a fitting groove with a T-shaped cross-section along a length direction of the connecting piece; and a gradient of the inner side of the connecting piece is equal to a generatrix inclination of the lower half of the spinning shaft;
   four notches are arranged at a bottom of the circular receiving groove for partial passage of the four connecting pieces; and the inner side of the connecting piece passes through the notch to be located inside the shear cylinder;
   a conical surface on the lower half of the spinning shaft is provided with four guide rail strips, wherein the four guide rail strips are circularly spaced around an axis of the spinning shaft; and a length direction of each of the guide rail strips is oriented from a major-diameter end on the lower half of the spinning shaft towards a minor-diameter end on the lower half of the spinning shaft; and
   each of the guide rail strips is provided with a T-shaped cross-section and matched with one connecting piece; and the guide rail strip is slidably provided in the fitting groove.

2. The borehole wall spin-shearing device for the in-situ borehole shear test according to claim 1, wherein a plurality of limit bars are circularly evenly spaced on a circumferential outer wall on the upper half of the spinning shaft within the shear cylinder; and the plurality of limit bars are detachably connected to the circumferential outer wall on the upper half of the spinning shaft; and
   the shear cylinder is provided with two open ends; a circumferential inner wall of the shear cylinder is provided with a plurality of limit slots, wherein the plurality of limit slots are slidably matched with the plurality of limit bars; and the plurality of limit bars and the plurality of limit slots are arranged along an axial direction of the spinning shaft.

3. The borehole wall spin-shearing device for the in-situ borehole shear test according to claim 2, wherein a top opening of the shear cylinder is provided with a limit flange; and an inner ring diameter of the limit flange is greater than a diameter of the upper half of the spinning shaft and smaller than an inner diameter of the shear cylinder.

4. The borehole wall spin-shearing device for the in-situ borehole shear test according to claim 3, wherein a bottom opening of the shear cylinder is provided with a rebound assembly; the rebound assembly comprises a spring sleeve; the spring sleeve comprises a top end with an opening and a closed bottom end; the top end of the spring sleeve is connected to a bottom of the shear cylinder; a reset spring is provided in the spring sleeve; a bottom end of the reset spring is fixedly connected to an inner bottom side of the spring sleeve; and a top of the reset spring is fixed to a push plate; and when the drill rod presses downwards, the lower half of the spinning shaft is driven to pass through the top opening of the spring sleeve to contact an upper end face of the push plate.

5. The borehole wall spin-shearing device for the in-situ borehole shear test according to claim 4, wherein a bottom of the spring sleeve is provided with a rotating base in a cylindrical structure; an axis of the rotating base coincides with an axis of the spring sleeve; a threaded cylindrical pin is provided in the spring sleeve; an axis of the threaded cylindrical pin coincides with the axis of the spring sleeve; a threaded end of the threaded cylindrical pin passes through the bottom end of the spring sleeve and is matched with a center thread of the rotating base; a plain shaft portion of the threaded cylindrical pin is rotatably matched with the bottom end of the spring sleeve; and a thrust bearing is provided between the rotating base and the spring sleeve.

6. A testing method for the borehole wall spin-shearing device for the in-situ borehole shear test according to claim 1, comprising the following steps:

step 1: drilling, by the drilling rig, a borehole;

step 2: calibrating the soil shearing assembly on a ground: applying, by the drill rod, the vertical load; and measuring, by the data acquisition assembly, load values required to eject the plurality of shear plates;

step 3: connecting the drill rod to the soil shearing assembly, and putting the soil shearing assembly to a preset test depth in the borehole, such that a bottom of the soil shearing assembly comes into contact with soil at a bottom surface of the borehole;

step 4: continuously pressing the drill rod downwards to apply the vertical load to the plurality of shear plates in the soil shearing assembly, such that the plurality of shear plates are ejected due to the vertical load and fully penetrate into the undisturbed soil;

step 5: keeping an axial direction of the drill rod constant; starting the servo motor to drive the drill rod to rotate, such that the plurality of shear plates in the soil shearing assembly conduct a borehole wall spin-shearing test; and stopping the borehole wall spin-shearing test after the plurality of shear plates rotate 90°; and step 6: performing, by the data acquisition assembly comprising a torque sensor and a pressure sensor, the following operations: acquiring, by the torque sensor, maximum torques applied to the plurality of shear plates during the borehole wall spin-shearing test; acquiring, by the pressure sensor, maximum normal forces received by the plurality of shear plates; and calculating a shear strength parameter of the undisturbed soil based on the maximum torques and the maximum normal forces.

7. The testing method for the borehole wall spin-shearing device for the in-situ borehole shear test according to claim 6, wherein in the step 6, the shear strength parameter of the undisturbed soil is calculated as follows:

$$\tau_{max} = \frac{4M_{T_{max}}}{\pi D^2 h}$$

wherein, $\tau_{max}$ denotes a maximum shear stress of the undisturbed soil, and is measured in kPa; $M_{T_{max}}$ denotes a maximum torque applied to a single shear unit, and is measured in kN·m; and D and h respectively denote a diameter and a height of a circular arc formed by a rotation of the plurality of shear plates ejected, and are measured in m;

at a same depth in four adjacent boreholes, maximum shear stresses of the undisturbed soil at the same depth in four different boreholes are expressed as $\tau_{max1}$–$\tau_{max4}$, and the maximum normal forces acquired by the pressure sensor are expressed as $\sigma_{nmax1}$–$\sigma_{nmax4}$;

$$\tau_{max} = c + \sigma_{nmax} \tan \varphi$$

the maximum normal forces $\sigma_{nmax1}$–$\sigma_{nmax4}$ are measured in kPa; a curve is plotted with the maximum normal force $\sigma_{nmax}$ as an x-axis and the maximum shear stress $\tau_{max}$ as a y-axis; and shear strength parameters c and φ are acquired through curve fitting; c denotes cohesion, and is measured in kPa; φ denotes an internal friction angle; and the cohesion and the internal friction angle are the shear strength parameters of the undisturbed soil.

8. The testing method according to claim 6, wherein in the borehole wall spin-shearing device for the in-situ borehole shear test, a plurality of limit bars are circularly evenly spaced on a circumferential outer wall on the upper half of the spinning shaft within the shear cylinder; and the plurality of limit bars are detachably connected to the circumferential outer wall on the upper half of the spinning shaft; and the shear cylinder is provided with two open ends; a circumferential inner wall of the shear cylinder is provided with a plurality of limit slots, wherein the plurality of limit slots are slidably matched with the plurality of limit bars; and the plurality of limit bars and the plurality of limit slots are arranged along an axial direction of the spinning shaft.

9. The testing method according to claim 8, wherein in the borehole wall spin-shearing device for the in-situ borehole shear test, a top opening of the shear cylinder is provided with a limit flange; and an inner ring diameter of the limit flange is greater than a diameter of the upper half of the spinning shaft and smaller than an inner diameter of the shear cylinder.

10. The testing method according to claim 9, wherein in the borehole wall spin-shearing device for the in-situ borehole shear test, a bottom opening of the shear cylinder is provided with a rebound assembly; the rebound assembly comprises a spring sleeve; the spring sleeve comprises a top end with an opening and a closed bottom end; the top end of the spring sleeve is connected to a bottom of the shear cylinder; a reset spring is provided in the spring sleeve; a bottom end of the reset spring is fixedly connected to an inner bottom side of the spring sleeve; and a top of the reset spring is fixed to a push plate; and when the drill rod presses downwards, the lower half of the spinning shaft is driven to pass through the top opening of the spring sleeve to contact an upper end face of the push plate.

11. The testing method according to claim 10, wherein in the borehole wall spin-shearing device for the in-situ borehole shear test, a bottom of the spring sleeve is provided with a rotating base in a cylindrical structure; an axis of the rotating base coincides with an axis of the spring sleeve; a threaded cylindrical pin is provided in the spring sleeve; an axis of the threaded cylindrical pin coincides with the axis of the spring sleeve; a threaded end of the threaded cylindrical pin passes through the bottom end of the spring sleeve and is matched with a center thread of the rotating base; a plain shaft portion of the threaded cylindrical pin is rotatably matched with the bottom end of the spring sleeve; and a thrust bearing is provided between the rotating base and the spring sleeve.

* * * * *